US012609186B2

(12) United States Patent
Blevins et al.

(10) Patent No.: US 12,609,186 B2
(45) Date of Patent: Apr. 21, 2026

(54) TECHNIQUES FOR DATA-ENABLED DRUG DISCOVERY

(71) Applicant: RECURSION PHARMACEUTICALS, INC., Salt Lake City, UT (US)

(72) Inventors: Andrew Blevins, Salt Lake City, UT (US); Jorge Aguilera-Iparraguirre, Jamaica Plain, MA (US); Mika Lindvall, Salt Lake City, UT (US)

(73) Assignee: RECURSION PHARMACEUTICALS, INC., Salt Lake City, UT (US)

( * ) Notice: Subject to any disclaimer, the term of this patent is extended or adjusted under 35 U.S.C. 154(b) by 782 days.

(21) Appl. No.: 16/950,845

(22) Filed: Nov. 17, 2020

(65) Prior Publication Data

US 2022/0059195 A1    Feb. 24, 2022

Related U.S. Application Data

(60) Provisional application No. 63/067,025, filed on Aug. 18, 2020.

(51) Int. Cl.
*G16C 20/50* (2019.01)
*G16C 20/40* (2019.01)
*G16C 20/70* (2019.01)

(52) U.S. Cl.
CPC ............. *G16C 20/50* (2019.02); *G16C 20/40* (2019.02); *G16C 20/70* (2019.02)

(58) Field of Classification Search
None
See application file for complete search history.

(56) References Cited

U.S. PATENT DOCUMENTS

2003/0009298 A1    1/2003  Pitman et al.
2008/0234135 A1*   9/2008  Ghosh .................... G16C 20/50
                                                      506/8

(Continued)

FOREIGN PATENT DOCUMENTS

CN        109841263 A      6/2019
CN        110851617 A      2/2020

(Continued)

OTHER PUBLICATIONS

Liu, X., Ouyang, S., Yu, B., Liu, Y., Huang, K., Gong, J., . . . & Jiang, H. (2010). PharmMapper server: a web server for potential drug target identification using pharmacophore mapping approach. Nucleic acids research, 38(suppl_2), W609-W614. (Year: 2010).*

(Continued)

*Primary Examiner* — Karlheinz R. Skowronek
*Assistant Examiner* — Mary C Leverett
(74) *Attorney, Agent, or Firm* — Artegis Law Group, LLP

(57)            ABSTRACT
In various embodiments, a molecule exploration application determines one or more potential drug candidates during a drug discovery process. The molecule exploration application generates derived molecule specifications based on a query molecule specification and edit heuristics. Subsequently, the molecule exploration application performs, via a mapping algorithm, one or more mapping operations on the derived molecule specifications to generate mapped molecule specifications. The molecule exploration application then performs one or more search operations on a mapped catalog of molecules based on the mapped molecule specifications to determine the one or more potential drug candidates. Advantageously, the molecule exploration application can be used to efficiently determine additional drug development candidates during a drug discovery process.

20 Claims, 4 Drawing Sheets

(56) References Cited

U.S. PATENT DOCUMENTS

| | | | | |
|---|---|---|---|---|
| 2009/0319547 | A1* | 12/2009 | Hollis | G06F 16/1744 |
| 2010/0305930 | A1* | 12/2010 | Ho | G16C 20/50 |
| | | | | 703/11 |
| 2012/0009277 | A1 | 1/2012 | Sardari et al. | |
| 2014/0052755 | A1* | 2/2014 | Pitman | B60G 3/20 |
| | | | | 707/771 |
| 2014/0171332 | A1 | 6/2014 | Katz et al. | |
| 2019/0221291 | A1 | 7/2019 | Grisham et al. | |

FOREIGN PATENT DOCUMENTS

| | | |
|---|---|---|
| CN | 111415702 A | 7/2020 |
| JP | 2013-191068 A | 9/2013 |
| JP | 2018-537653 A | 12/2018 |
| JP | 2021-516330 A | 7/2021 |
| WO | 2017/041016 A1 | 3/2017 |
| WO | 2019/178610 A1 | 9/2019 |

OTHER PUBLICATIONS

Baldi, A. (2010). Computational approaches for drug design and discovery: An overview. Systematic reviews in Pharmacy, 1(1), 99. (Year: 2010).*

Kind, Tobias, and Oliver Fiehn. "Seven Golden Rules for heuristic filtering of molecular formulas obtained by accurate mass spectrometry." BMC bioinformatics 8 (2007): 1-20. (Year: 2007).*

International Search Report for application No. PCT/US2021/046209 dated Nov. 22, 2021.

Yu, Yun William, "Compressive Algorithms for Search and Storage In Biological Data", Jun. 2017, 197 pages.

Extended European Search Report for Application No. 21858925.7 dated Dec. 10, 2024.

Stewart et al., "Drug Guru: A Computer Software Program for Drug Design Using Medicinal Chemistry Rules", Bioorganic & Medicinal Chemistry, vol. 14, DOI:10.1016/j.bmc.2006.06.024, Oct. 15, 2006, pp. 7011-7022.

Raymond et al., "Rationalizing Lead Optimization by Associating Quantitative Relevance with Molecular Structure Modification", Journal of Chemical Information and Modeling, vol. 49, DOI:10.1021/ci9000426, Jul. 15, 2009, pp. 1952-1962.

Miller, Mitchell A., "Chemical Database Techniques in Drug Discovery", Nature Reviews, DOI:10.1038/nrd745, vol. 1, Mar. 1, 2002, pp. 220-227.

Ihlenfeldt et al., "Hash Codes for the Identification and Classification of Molecular Structure Elements", Journal of Computational Chemistry, DOI:10.1002/JCC.540150802, vol. 15, No. 8, Jan. 1, 1994, pp. 793-813.

Boucher et al., "What on Earth is InChl?", retrieved from https://iupac.org/100/stories/what-on-earth-is-inchi/, Feb. 1, 2018, 7 pages.

Zhang et al., "Construction of a Virtual Combinatorial Fragment Library Based on Drug Data Reporting Databases", vol. 37, No. 3, Science In China Press, Jun. 2007, pp. 288-294.

* cited by examiner

Figure 3:
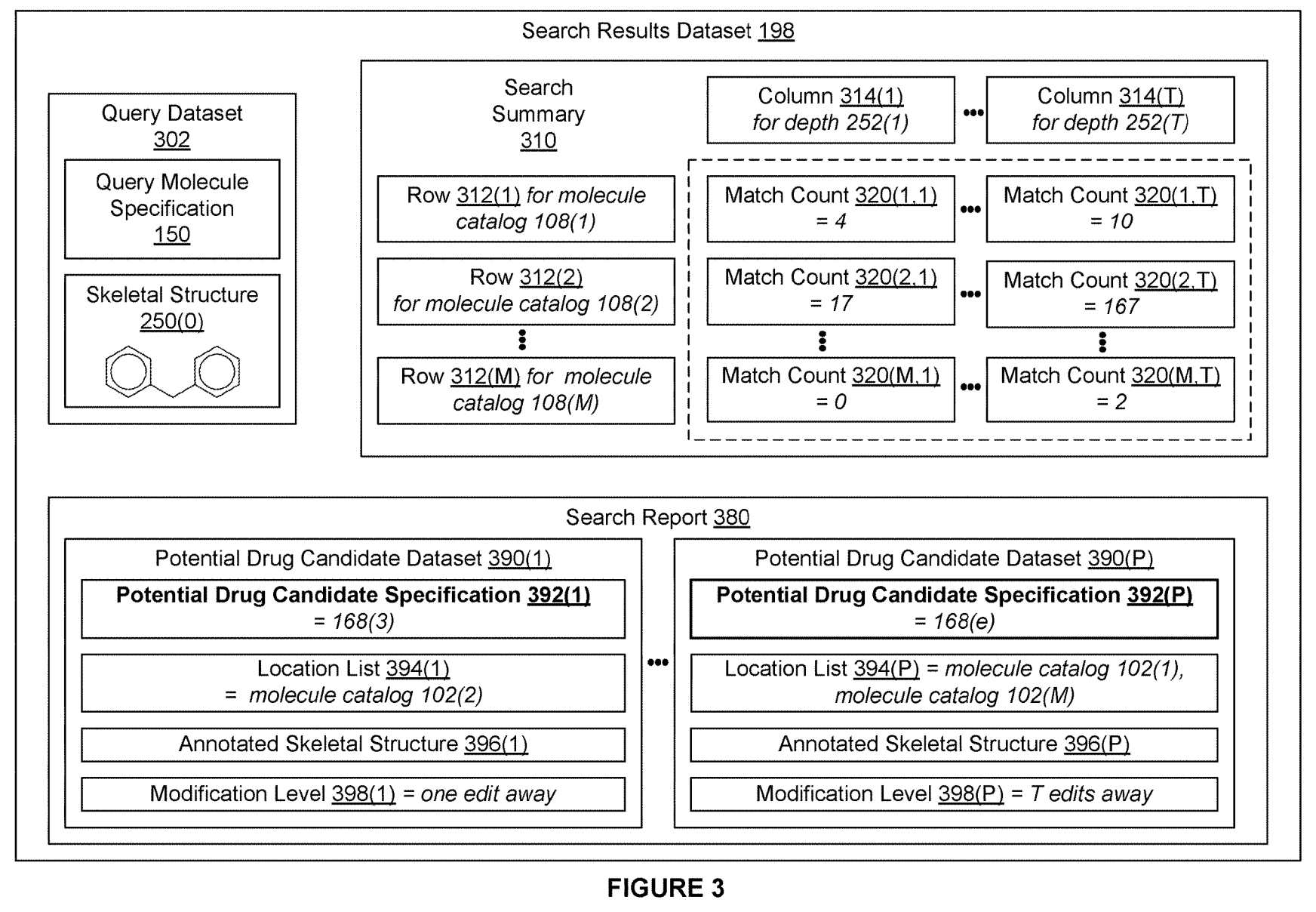

Query Dataset 302

Query Molecule Specification 150

Skeletal Structure 250(Q)

Search Results Dataset 198

Search Summary 310

| Column 314(1) for depth 252(1) | ... | Column 314(T) for depth 252(T) |
|---|---|---|
| Match Count 320(1,1) = 4 | ... | Match Count 320(1,T) = 10 |
| Match Count 320(2,1) = 17 | ... | Match Count 320(2,T) = 167 |
| Match Count 320(M,1) = 0 | ... | Match Count 320(M,T) = 2 |

Row 312(1) for molecule catalog 108(1)

Row 312(2) for molecule catalog 108(2)

Row 312(M) for molecule catalog 108(M)

Search Report 380

Potential Drug Candidate Dataset 390(1)

Potential Drug Candidate Specification 392(1) = 168(3)

Location List 394(1) = molecule catalog 102(2)

Annotated Skeletal Structure 396(1)

Modification Level 398(1) = one edit away

Potential Drug Candidate Dataset 390(P)

Potential Drug Candidate Specification 392(P) = 168(e)

Location List 394(P) = molecule catalog 102(1), molecule catalog 102(M)

Annotated Skeletal Structure 396(P)

Modification Level 398(P) = T edits away

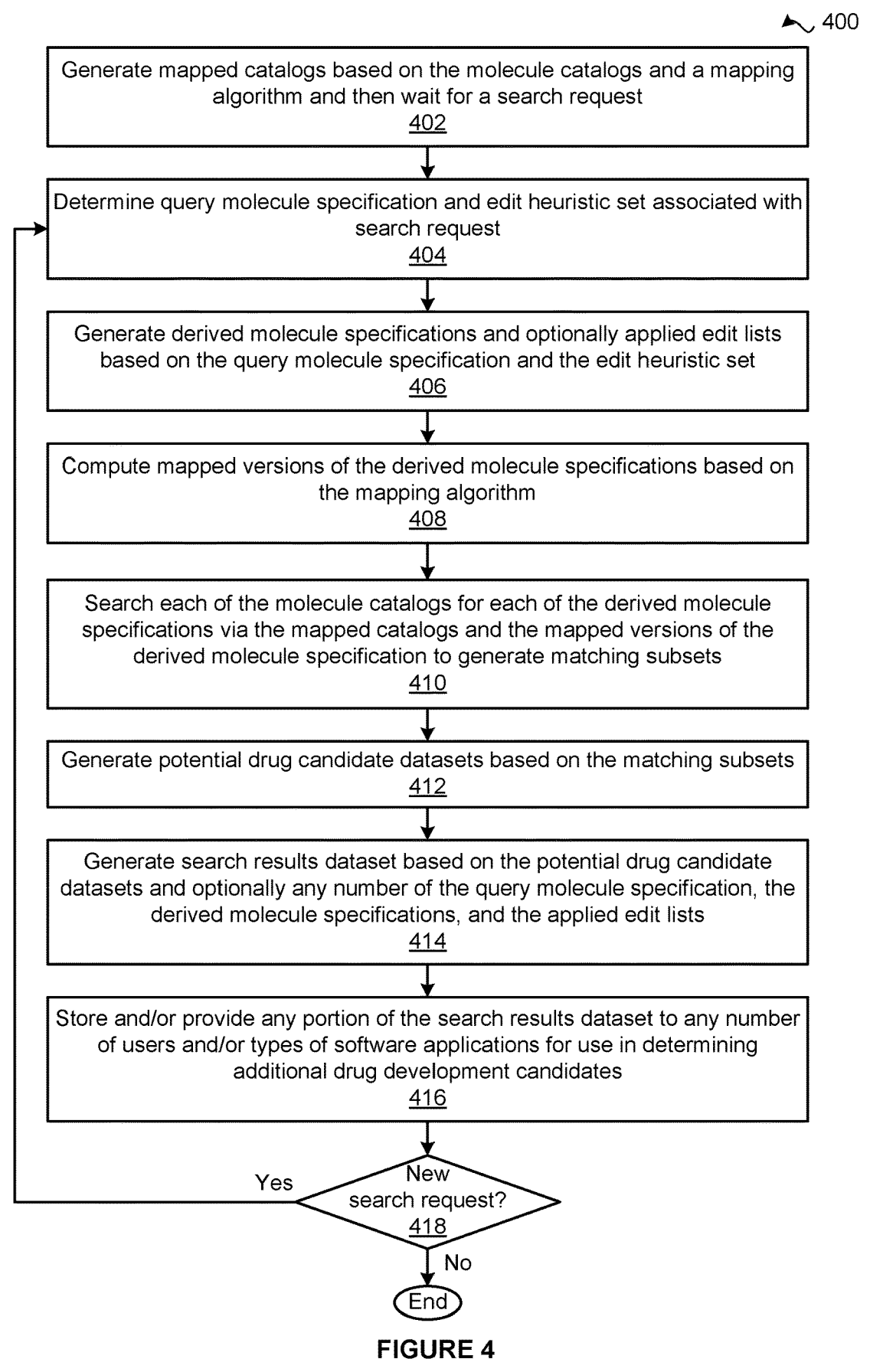

Generate mapped catalogs based on the molecule catalogs and a mapping algorithm and then wait for a search request
402

Determine query molecule specification and edit heuristic set associated with search request
404

Generate derived molecule specifications and optionally applied edit lists based on the query molecule specification and the edit heuristic set
406

Compute mapped versions of the derived molecule specifications based on the mapping algorithm
408

Search each of the molecule catalogs for each of the derived molecule specifications via the mapped catalogs and the mapped versions of the derived molecule specification to generate matching subsets
410

Generate potential drug candidate datasets based on the matching subsets
412

Generate search results dataset based on the potential drug candidate datasets and optionally any number of the query molecule specification, the derived molecule specifications, and the applied edit lists
414

Store and/or provide any portion of the search results dataset to any number of users and/or types of software applications for use in determining additional drug development candidates
416

Yes

New search request?
418

No

End

FIGURE 4

TECHNIQUES FOR DATA-ENABLED DRUG DISCOVERY

CROSS-REFERENCE TO RELATED APPLICATIONS

This application claims priority benefit of the United States Provisional Patent Application titled, "Real-Time SAR Search Tool for Very Large Compound Databases," filed on Aug. 18, 2020 and having Ser. No. 63/067,025. The subject matter of this related application is hereby incorporated herein by reference.

FIELD OF THE VARIOUS EMBODIMENTS

The various embodiments relate generally to computer science and biochemical analysis and, more specifically, to techniques for data-enabled drug discovery.

DESCRIPTION OF THE RELATED ART

Drug discovery is the process by which molecules for curing, mitigating, treating, and/or preventing diseases are identified for further investigation. During the initial phase of a typical drug discovery process, many different molecules are tested to determine a drug development candidate of interest that has a desired effect on cells (referred to as exhibiting a "target bioactivity"). For example, a drug development candidate of interest could be a drug that increases the health of cells afflicted with a particular disease. Based on the principle that structurally similar molecules often share some similar bioactivities, after identifying a given drug development candidate of interest, any number of molecule catalogs of available molecules are searched for molecules that are structurally similar to the drug development candidate of interest. The molecules specified in the search results become potential drug candidates that are then evaluated to identify additional drug development candidates, where each additional drug development candidate has the same bioactivity as the drug development candidate of interest. As a general matter, any of the additional drug development candidates identified using the process could have improved physical, chemical, biological, and/or pharmacological properties relative to the drug development candidate of interest.

In one approach to determining potential drug candidates, a similarity software application quantifies the structural similarity between the drug development candidate of interest and each of the molecules specified in any number of molecule catalogs based on a similarity metric. In some implementations, the similarity software application computes values of a Tanimoto coefficient that quantifies the structural similarity between two molecules based on a set of molecular structural fragments. In such implementations, for each molecule specified in the search results, the similarity software application sets the value for the Tanimoto coefficient equal to the ratio of the number of molecular structural fragments shared between the molecule and the drug development candidate of interest to the number of molecular structural fragments existing in either or both of the molecule and the drug development candidate of interest. Subsequently, the similarity software application generates search results specifying the molecules that have values for the Tanimoto coefficient that exceed a minimum similarity threshold. Any molecule having a Tanimoto coefficient that exceeds the minimum similarity threshold is considered to be a potential drug candidate.

One drawback of determining potential drug candidates based on similarity metrics is that different drugs having "similar" molecular structures as per similarity metrics do not necessarily share a given bioactivity. Thus, for a given drug discovery process, the fraction of the potential drug candidates identified using a particular similarity metric that have the same target bioactivity as the relevant drug development candidate of interest can be quite low. As a result, oftentimes substantial amounts of time and resources are wasted evaluating potential drug candidates that ultimately are irrelevant to the given drug discovery process.

Another drawback of determining potential drug candidates based on similarity metrics is that, because the computational complexity of the catalog searches scales with the total number of available molecules, the amounts of time and computational resources required to comprehensively search the molecule catalogs can be quite prohibitive. For example, evaluating the hundreds of millions of available molecules included in current molecule catalogs using a three-dimensional shape-based similarity metric can require decades of compute time. Oftentimes, because of time and computational resource constraints, only a fraction of the molecules specified in current molecule catalogs are searched during a given drug discovery process.

As the foregoing illustrates, what is needed in the art are more effective techniques for determining potential drug candidates during drug discovery processes.

SUMMARY

One embodiment of the present invention sets forth a method for determining one or more potential drug candidates during a drug discovery process. The method includes generating derived molecule specifications based on a query molecule specification and edit heuristics; performing, via a mapping algorithm, one or more mapping operations on the derived molecule specifications to generate mapped molecule specifications; and performing one or more search operations on a mapped catalog of molecules based on the mapped molecule specifications to determine the one or more potential drug candidates.

At least one technical advantage of the disclosed techniques relative to the prior art is that the disclosed techniques can be used to more efficiently determine additional drug development candidates during a drug discovery process. In that regard, because the relevant edit heuristics implemented using the disclosed techniques are tailored for a given drug discovery process, the likelihood that the structural changes introduced by those edit heuristics preserve the target bioactivity is increased. Consequently, the proportion of structurally similar drug candidates identified using the disclosed techniques that ultimately are relevant to the given drug discovery process is typically increased relative to prior art approaches. Furthermore, unlike prior art techniques, because the computational complexity of the disclosed techniques remains constant regardless of the total number of molecules being searched, the amounts of time and computational resources required to comprehensively search the molecule catalogs can be reduced. In particular, with the disclosed techniques, all of the available molecules can be searched at a given interactive rate. These technical advantages provide one or more technological improvements over prior art approaches.

BRIEF DESCRIPTION OF THE DRAWINGS

So that the manner in which the above recited features of the various embodiments can be understood in detail, a more particular description of the inventive concepts, briefly summarized above, may be had by reference to various embodiments, some of which are illustrated in the appended drawings. It is to be noted, however, that the appended drawings illustrate only typical embodiments of the inventive concepts and are therefore not to be considered limiting of scope in any way, and that there are other equally effective embodiments.

FIG. 3 is a more detailed illustration of the search results dataset of FIG. 1, according to various embodiments; and FIG. 4 is a flow diagram of method steps for determining potential drug candidates during a drug discovery process, according to various embodiments.

DETAILED DESCRIPTION

Figure 1:
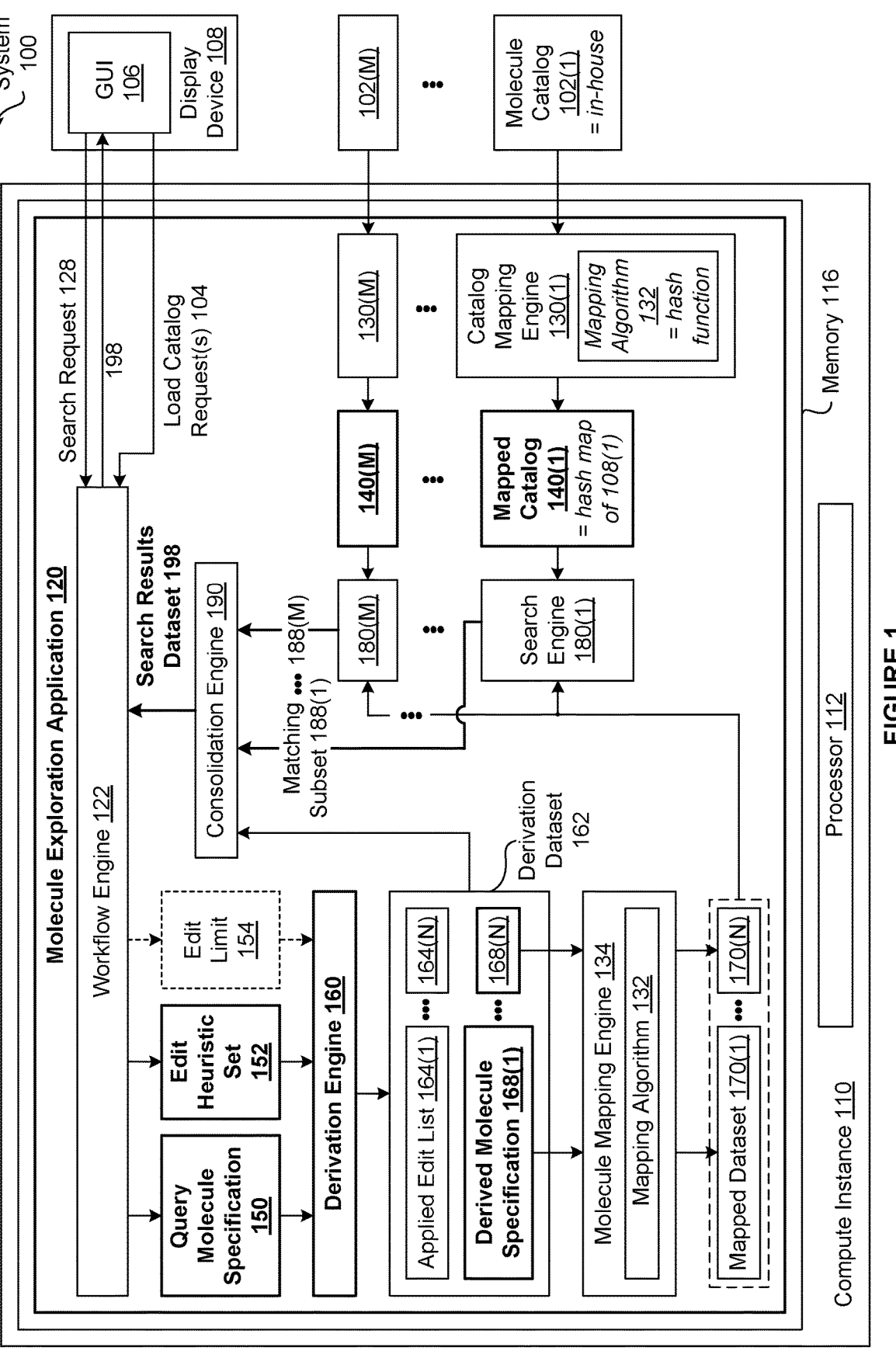
FIG. 1 is a conceptual illustration of a system configured to implement one or more aspects of the various embodiments.

In the following description, numerous specific details are set forth to provide a more thorough understanding of the various embodiments. However, it will be apparent to one skilled in the art that the inventive concepts may be practiced without one or more of these specific details.

Exemplary Overview

For explanatory purposes only, an overview of an exemplary embodiment is described herein. In some embodiments, the disclosed techniques can be used to efficiently derive potential drug candidates from drug development candidates of interest during drug discovery processes. The potential drug candidates can then be evaluated to determine which of the potential drug candidates are additional drug development candidates. For a given drug discovery process, each drug development candidate (e.g., a drug development candidate of interest or an additional drug development candidate) is a molecule that has a desired effect on cells that is aligned with the overall goal of the drug discovery process. The desired effect on cells is also referred to herein as a "target bioactivity." For example, each drug development candidate could increase the health of cells afflicted with a particular disease.

In an initialization phase, a molecule exploration application applies a hash function to any number of molecule catalogs to generate mapped catalogs. Each of the molecule catalogs includes available molecule specifications representing any number of available molecules. The hash function maps a molecule specification (i.e., a "key") to an array index. Each mapped catalog is a hash map of an associated molecule catalog that stores the available molecule specifications included in the molecule catalog in buckets based on the associated array indices.

During a subsequent search phase, the molecule exploration application receives any number of search requests, where each search request is associated with a query molecule specification and any number of edit heuristics. A query molecule specification is a representation of a molecule referred to herein as a "query molecule." In some embodiments, the query molecule is a drug development candidate of interest that has a target bioactivity. Each edit heuristic specifies a different type of modification to the structure of an existing molecule. The edit heuristics are typically designed to have some relevance to one or more drug discovery processes.

In particular, for each of at least one of the edit heuristics, relative to a random structural modification, empirical evidence shows that the structural modification specified by the edit heuristic is more likely to preserve target bioactivities associated with typical drug discovery processes. In other words, when applied to a query molecule specification associated with a target bioactivity, at least one of the edit heuristics is designed to preferentially produce a derived molecule specification that is also associated with the target bioactivity.

In response to a given search request, the molecule exploration application iteratively applies the associated edit heuristics to the associated query molecule specification to generate derived molecule specifications representing all possible combinations of the edit heuristics. The molecule exploration application then applies the hash function to the derived molecule specifications to generate corresponding array indices. For each of the mapped catalogs, the molecule exploration application searches for each of the derived molecule specifications based on the corresponding array index to generate a matching subset. Each of the matching subsets specifies, without limitation, the derived molecule specifications that exist in the associated molecule catalog.

Subsequently, the molecule exploration application generates a search results dataset based on the matching subsets. The search results dataset includes, without limitation, a search report specifying each of the derived molecule specifications that exist in at least one of the molecule catalogs and the associated location(s) (i.e., the associated molecule catalog(s)). Each of the derived molecule specifications included in the search report represents a different potential drug candidate. The search results dataset can include any amount and/or types of additional data that is relevant to the drug discovery process. The molecule exploration application then stores and/or provides any portion of the search results dataset to any number of other software applications and/or users for use in determining additional drug development candidates.

System Overview

FIG. 1 is a conceptual illustration of a system 100 configured to implement one or more aspects of the various embodiments. For explanatory purposes, multiple instances of like objects are denoted with reference numbers identifying the object and parenthetical alphanumeric character(s) identifying the instance where needed. As shown, the system 100 includes, without limitation, a compute instance 110, a display device 108, and molecule catalogs 102(1)-102(M), where M can be any positive integer.

In some embodiments, the system 100 can include, without limitation, any number of compute instances 110, any number (including zero) of display devices 108, and any number of molecule catalogs 102 in any combination. The components of the system 100 can be distributed across any number of shared geographic locations and/or any number of different geographic locations and/or implemented in one or more cloud computing environments (i.e., encapsulated shared resources, software, data, etc.) in any combination.

As shown, the compute instance 110 includes, without limitation, a processor 112 and a memory 116. The compute instance 110 can be implemented in a cloud computing environment, implemented as part of any other distributed computing environment, or implemented in a stand-alone fashion. In some embodiments, each of any number of compute instances 110 can include any number of processors 112 and any number of memories 116 in any combination. In the same or other embodiments, any number of compute instances 110 (including one) can provide a multiprocessing environment in any technically feasible fashion. The compute instance 110 is also referred to herein as "a computing device."

The processor 112 can be any instruction execution system, apparatus, or device capable of executing instructions. For example, the processor 112 could comprise a central processing unit, a graphics processing unit, a controller, a micro-controller, a state machine, or any combination thereof. The memory 116 of the compute instance 110 stores content, such as software applications and data, for use by the processor 112 of the compute instance 110. The memory 116 can be one or more of a readily available memory, such as random-access memory, read only memory, floppy disk, hard disk, or any other form of digital storage, local or remote.

In some embodiments, a storage (not shown) can supplement or replace the memory 116. The storage can include any number and type of external memories that are accessible to the processor 112. For example, and without limitation, the storage can include a Secure Digital Card, an external Flash memory, a portable compact disc read-only memory, an optical storage device, a magnetic storage device, or any suitable combination of the foregoing.

In some embodiments, the compute instance 110 can be associated with any number (including zero) and/or types of input devices, output devices, and/or input/output devices in any combination. An input device is any device that is capable of receiving input from users. Some examples of input devices include, without limitation, keyboards, mice, trackpads, microphones, video cameras, etc. An output device is any device that is capable of providing output to users. Some examples of output devices include, without limitation, the display device 108, headphones, speakers, etc. An input/output device is any device that is capable of both receiving input from users and providing output to users, such as a touchscreen.

As shown, in some embodiments, the compute instance 110 is associated with the display device 108. The display device 108 can be any device that is capable of displaying an image and/or any other type of visual content. For example, the display device 108 could be, without limitation, a liquid crystal display, a light-emitting diode display, a projection display, a plasma display panel, etc. In some embodiments, the display device 108 is a touchscreen that is capable of displaying visual content and receiving input (e.g., from a user).

In some embodiments, the compute instance 110 can be integrated with any number and/or types of other devices (e.g., other compute instances 110, input devices, output devices, input/output devices, etc.) into a user device. Some examples of user devices include, without limitation, desktop computers, laptops, smartphones, smart televisions, game consoles, tablets, etc.

In general, the compute instance 110 is configured to implement one or more software applications. For explanatory purposes only, each software application is described as residing in the memory 116 of the compute instance 110 and executing on the processor 112 of the compute instance 110. However, in some embodiments, the functionality of each software application can be distributed across any number of other software applications that reside in the memories 116 of any number of compute instances 110 and execute on the processors 112 of any number of compute instances 110 in any combination. Further, the functionality of any number of software applications can be consolidated into a single software application.

In some embodiments, any number of software applications and/or portions of software applications are stored in one or more non-transitory computer readable media. The term "non-transitory," as used herein, is a limitation of the medium itself (i.e., tangible, not a signal) as opposed to a limitation on data storage persistency (e.g., random access memory versus read-only memory). Non-transitory computer readable media are also referred to herein "computer readable media." For instance, in some embodiments, the memory 116 is a computer readable medium, and any number of software applications and/or portions of software applications are stored in the memory 116.

In some embodiments, any number of software applications and/or portions of software applications are stored in one or more computer readable media prior to being stored in the memory 116. For instance, in some embodiments, any number of software applications and/or portions of software applications are stored on a machine (e.g., a server machine), and any number of the software applications and/or the portions of the software applications are downloaded from the machine to the memory 116. In the same or other embodiments, any number of software applications and/or portions of software applications are stored in some form of portable computer readable medium, and any number of the applications and/or the portions of the applications are downloaded from the portable computer readable medium to the memory 116. Some examples of portable computer readable media includes, without limitation, digital video discs, memory discs, memory sticks, etc.

In some embodiments, aspects of the present disclosure can take the form a computer program product embodied in one or more computer readable media having computer readable program codec embodied thereon. Any combination of one or more computer readable media can be utilized. Each computer readable medium can be a computer readable signal medium or a computer readable storage medium. A computer readable storage medium can be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory, a read-only memory, an erasable programmable read-only memory, a Flash memory, an optical fiber, a portable compact disc read-only memory, an optical storage device, a magnetic storage device, or any suitable combination of the foregoing. In the context of this document, a computer readable storage medium can be any tangible medium that can contain or store a program for use by or in connection with an instruction execution system, apparatus, or device.

In some embodiments, the compute instance 110 is configured to determine potential drug candidates based on drug development candidates of interest during drug discovery processes, thereby facilitating the identification of additional drug development candidates. A "drug development candidate" is a molecule that has a target effect on cells referred to herein as a "target bioactivity." An example of a target bioactivity is increasing the health of cells afflicted with a particular disease. Each drug development candidate of interest can be any drug development candidate that has been identified in any technically feasible fashion (e.g., via laboratory testing). For example, a drug development candidate of interest can be identified during an assay that measures cell proliferation or dying. In another example, a drug development candidate of interest can be identified during an assay that looks for the presence of a particular biomarker (e.g., the amount of a particular cytokine that cells excrete). In yet another example, a drug development candidate can be identified during an assay that looks for positive effects in a model organism.

As referred to herein, an "additional drug development candidate" refers to a drug development candidate that is determined based an associated drug development candidate of interest. Each "potential drug candidate" is a molecule that is structurally similar to an associated drug development candidate of interest and could have the same target bioactivity as the associated drug development candidate of interest. In some embodiments, a subset of the potential drug candidates are subsequently determined to be additional drug development candidates.

In some embodiments, each of the additional drug development candidates is specified in at least one of the molecule catalogs 102(1)-102(M). For explanatory purposes only, the molecule catalogs 102(1)-102(M) are also referred to herein individually as "the molecule catalog 102" and collectively as "the molecule catalogs 102." The molecule catalog 102 is also referred to herein as "a catalog of molecules." In some embodiments, M is equal to 1, and the system 100 includes, without limitation, the molecule catalog 102(1).

Each of the molecule catalogs 102 includes, without limitation, any number of available molecule specifications (not shown). Each available molecule specification is a structural representation of a molecule that can be acquired (e.g., ordered, generated, etc.) in any technically feasible fashion. As referred to herein, a structural representation of a molecule specifies, without limitation, which atoms are bonded to one another and optionally any amount of additional structural information. For instance, some structural representations of a molecule include additional structural information that specifies the approximate spatial arrangement of the atoms in the molecule and/or any lone pairs of electrons that can exist in the molecule.

In some embodiments, a structural representation of a given molecule can any of a Simplified Molecular Input Line Entry Specification ("SMILES") string, an International Union of Pure and Applied Chemistry ("IUPAC") International Chemical Identifier ("InChI"), a skeletal structure, etc. SMILES is a linear notation system that uses American Standard Code for Information Interchange characters to specify the structure of a given molecule as a SMILES string. An InChI is a textual identifier for a given molecule. A skeletal structure is a two-dimensional ("2D") graphic representation or "structural formula" that depicts, without limitation, how the atoms of a molecule can be arranged in 3D space.

As shown in italics, in some embodiments, the molecule catalog 102(1) is an in-house molecule catalog that includes, without limitation, any number of available molecule specifications that represent molecules that are available within an organization associated with the system 100. In the same or other embodiments, each of any number of the molecule catalogs 102 includes, without limitation, any number of available molecule specifications that represent molecules that can be ordered from an associated provider of molecules. In some embodiments, each of any number of the molecule catalogs 102 can specify any number and/or types of molecules and any amount and/or type of associated data describing how to acquire each of the molecules.

As described previously herein, in some conventional approaches to determining potential drug candidates, a conventional similarity software application searches molecule catalogs for potential drug candidates based on a similarity metric. Typically, for each of any number of the molecules specified in any number of molecule catalogs, the conventional similarity software application computes a value for the similarity metric based on the drug development candidate of interest and the molecule. The conventional software application then determines that the molecules associated with values for the similarity metric that exceed a minimum similarity threshold are potential drug candidates.

One drawback of determining potential drug candidates based on similarity metrics is that, for a given drug discovery process, the fraction of the potential drug candidates identified using a particular similarity metric that have the same target bioactivity as the drug development candidate of interest can be quite low. As a result, oftentimes substantial amounts of time and resources are wasted evaluating potential drug candidates that ultimately are irrelevant to the given drug discovery process.

Another drawback of determining potential drug candidates based on similarity metrics is that the computational complexity of the operations performed by the conventional similarity software application usually scale with the total number of available molecules. Consequently, the amounts of time and computational resources required to comprehensively search the molecule catalogs for potential drug candidates can be quite prohibitive.

Determining Potential Drug Candidates Based on Edit Heuristics

To address the above problems, the compute instance 110 includes, without limitation, a molecule exploration application 120 that automatically determines potential drug candidate specifications (not shown in FIG. 1) based on a query molecule specification 150, an edit heuristic set 152, and the molecule catalogs 102. As shown, in some embodiments, the molecule exploration application 120 resides in the memory 116 of the compute instance 110 and executes on the processor 112 of the compute instance 110.

For explanatory purpose only, in the embodiment depicted in FIG. 1, the molecule exploration application 120 initially operates in an initialization phase during which the molecule exploration application 120 receives any number and/or type of load catalog request(s) 104 and, in response, acquires and pre-processes the molecule catalogs 102(1)-102(M). Subsequently, the molecule exploration application 120 operates in a search phase during which the molecule exploration application 120 receives a search request 128 and, in response, generates a search results dataset 198.

In other embodiments, the molecule exploration application 120 can acquire and pre-process any subset (including the empty set) of the molecule catalogs 102 during the initialization phase and subsequently acquire and pre-process the remainder of molecule catalogs 102 on-demand during the search phase. In the same or other embodiments, the molecule exploration application 120 receives any number of search requests 128 during the search phase and, in response, generates any number of search results datasets 198.

As shown, in some embodiments, the molecule exploration application 120 includes, without limitation, a workflow engine 122, catalog mapping engines 130(1)-130(M), a derivation engine 160, a molecule mapping engine 134, search engines 180(1)-180(M), and a consolidation engine 190. The workflow engine 122 performs any number and/or types of input, output, translation, etc., operations and routes data to and from the inputs and outputs, respectively, of the catalog mapping engines 130(1)-130(M), the derivation engine 160, the molecule mapping engine 134, the search engines 180(1)-180(M), and the consolidation engine 190. The workflow engine 122 can receive input and provide output in any technically feasible fashion.

As shown, in some embodiments, the workflow engine 122 displays a graphical user interface ("GUI") 106 via the display device 108. The workflow engine 122 can receive number and/or types of inputs via the GUI 106 and can display any number and/or types of outputs via the GUI 106. In some embodiments, the workflow engine 122 receives the load catalog request(s) 104 and/or the search request 128 via the GUI 106. In the same or other embodiments, the workflow engine 122 displays a portion (including none or all) of the search results dataset 198 via the GUI 106.

In some embodiments, in response to the load catalog request(s) 104, the workflow engine 122 acquires the molecule catalogs 102 in any technically feasible fashion. To pre-process the molecule catalogs 102, the workflow engine 122 inputs available molecule specifications (not shown) included in the molecule catalogs 102(1)-102(M) into the catalog mapping engines 130(1)-130(M), respectively. In response, the catalog mapping engines 130(1)-130(M) output mapped catalogs 140(1)-140(M), respectively.

The catalog mapping engines 130(0)-130(M) are different instances of a single catalog mapping engine 130 (not explicitly shown). For explanatory purposes only, "the catalog mapping engine 130" as used herein refers to any instance of the catalog mapping engine 130, irrespective of whether the specific instance is depicted in any of the figures. The mapped catalogs 140(1)-140(M) are also referred to herein individually as "the mapped catalogs 140" and collectively as "the mapped catalog 140." The mapped catalog 140 is also referred to herein as "a mapped catalog of molecules."

In some other embodiments, the molecule exploration application 120 includes less than M instances of the catalog mapping engine 130, and the workflow engine 122 inputs the molecule catalogs 102(1)-102(M) into any number of instances of the catalog mapping engine 130 sequentially, concurrently, or in any combination thereof. For instance, in some embodiments, the workflow engine 122 sequentially inputs the molecule catalogs 102(1)-102(M) into a single instance of the catalog mapping engine 130. In response, the single instance of the catalog mapping engine 130 sequentially outputs the mapped catalogs 140(1)-140(M).

As shown explicitly for the catalog mapping engine 130(1), each of the catalog mapping engines 130(1)-130(M) includes, without limitation, a mapping algorithm 132. The catalog mapping engine 130($x$), for an integer x from 1 to M, performs mapping operations on each of the available molecule specifications included in the molecule catalog 102($x$) based on the mapping algorithm 132 to generate the mapped catalog 140($x$). The mapped catalog 140($x$) includes, without limitation, a mapped version of each of the available molecule specifications included in the molecule catalog 102($x$).

The mapping algorithm 132 can be any type of algorithm that, when applied to a molecule specification, generates a mapped version of the molecule specification. For explanatory purposes only, the mapped version of a molecule specification (including one of the available molecule specifications) is also referred to herein as a "mapped molecule specification." In some embodiments, the mapping algorithm 132 is associated with any number of mapping operations that, when the mapping algorithm 132 is applied to a molecule specification, map the molecule specification to a mapped molecule specification. The mapped molecule specification is a compressed digital representation of the molecule specification that facilitates search operations. The mapping algorithm 132 is compatible with at last one type of molecule specification (e.g., SMILES strings) and can generate at least one type of condensed digital representation of a molecule specification.

In some embodiments, the type of molecule specification that the molecule catalogs 102 use to represent the available molecules is compatible with the mapping algorithm 132. In some such embodiments, the catalog mapping engine 130($x$) applies the mapping algorithm 132 to each of the available molecule specifications included in the molecule catalog 102($x$) to generate the mapped versions of the available molecule specifications.

In some other embodiments, the type of molecule specification that the molecule catalogs 102 use to represent the available molecules is not compatible with the mapping algorithm 132. In some such embodiments, the workflow engine 122 and/or the catalog mapping engine 130 perform any number and/or type of translation operations on each of the available molecule specifications included in the molecule catalogs 102 to generate compatible versions of the molecule catalogs 102. The catalog mapping engine 130($x$) applies the mapping algorithm 132 to each of the available molecule specifications included in the compatible versions of the molecule catalog 102($x$) to generate the mapped versions of the available molecule specifications.

In some embodiments, the mapping algorithm 132 enables a specific type of search of the molecule catalogs 102. For instance, in some embodiments, the mapping algorithm 132 maps available molecule specifications to a vector space to enable a vector similarity search of the molecule catalogs 102 via the mapping algorithm 132 and the mapped catalogs 140. In the same or other embodiments, the mapping algorithm 132 ensures that the time required to search for molecule specifications in the molecule catalog 102 via the mapping algorithm 132 and the mapped catalog 102 is independent of the size of the mapped catalog 102.

In some embodiments, the mapping algorithm 132 exhibits any number and/or types of characteristics that are typically desirable for drug discovery processes. For instance, in some embodiments, the mapping algorithm 132 is tautomer friendly. As referred to herein, the mapping algorithm 132 is "tautomer friendly" if the mapping algorithm 132 attempts to detect and map different possible tautomeric forms of a molecule specification to single mapped version of the molecule specification.

As depicted in italics, in some embodiments, the mapping algorithm 132 is a hash function. The hash function maps a molecule specification (i.e., a "key") to an array index. The mapped catalog 140($x$), for an integer x from 1 to M, is therefore a hash map of the molecule catalog 102($x$). In some embodiments, the mapped catalog 140($x$) stores the available molecule specifications included in the molecule catalog 102($x$) based on the associated array indices. Advantageously, as persons skilled in the art will recognize, the time to look up a key via a hash function and a hash map is independent of the size of the hash map.

In some embodiments, the molecule catalog 102 represents available molecules as SMILES strings, and the mapping algorithm 132 is a tautomer friendly hash function that maps an InChI or a SMILES string to an InChIKey. An "InChIKey" encodes molecule specifications in a condensed, fixed-length format that is also commonly referred to as a "hashed InChI." Accordingly, in some embodiments, the mapped catalog 140(x), for an integer x from 1 to M, is a hash map that stores the SMILES strings included in the molecule catalog 102(x) based on the associated InChIKeys.

Although not shown, in some embodiments, after generating each of the mapped catalogs 140, the workflow engine 122 stores the mapped catalog 140 in any memory that is accessible to the molecule exploration application 120. In this fashion, one or more instances of the molecule exploration application 120 can generate the mapped catalogs 140 and other instances of the molecule exploration application 120 can reuse the mapped catalogs 140. In some embodiments, the workflow engine 122 can store the mapped catalogs 140 to memory in response to any number and/or types of requests and retrieve the mapped catalogs 140 from memory based on any number and/or types of requests.

During the search phase, the workflow engine 122 receives the search request 128 that is associated with a query molecule and, in response, determines the query molecule specification 150 and the edit heuristic set 152. The query molecule is a molecule that is to be the starting point of a search of the molecule catalogs 102. For instance, in some embodiments, the query molecule is a drug development candidate of interest in a drug discovery process and therefore the query molecule has an associated target bioactivity. The query molecule can be described and associated with the search request 128 in any technically feasible fashion.

The query molecule specification 150 is a structural representation of the query molecule in any format that is supported by the mapping algorithm 132 described previously herein. For instance, in some embodiments, the input to the mapping algorithm 132 is a SMILES string and therefore the query molecule specification 150 is a SMILES string that represents the query molecule. The workflow engine 122 performs any number and/or type of operations based on any description of the query molecule that is associated with the search request 128 to generate the query molecule specification 150.

For instance, in some embodiments, the search request 128 specifies a structural representation of the query molecule in a format that is supported by the mapping algorithm 132, and the workflow engine 122 sets the query molecule specification 150 equal to structural representation. In some other embodiments, the search request 128 is associated with a skeletal structure that graphically represents the query molecule, and the workflow engine 122 translates the skeletal structure to a structural representation of the query molecule in a format that is supported by the mapping algorithm 132

The edit heuristic set 152 includes, without limitation, any number and/or types of edit heuristics (not shown in FIG. 1). Each of the edit heuristics specifies a different type of modification to the structure of an existing molecule in any technically feasible fashion. For instance, in some embodiments, when applied to an existing molecule, one of the edit heuristics repositions any number of Nitrogens to generates any number (including zero) of isomers of the existing molecule that differ only in the position of a Nitrogen.

In some embodiments, the edit heuristics are designed to have some relevance to one or more drug discovery processes. In the same or other embodiments, for each of at least one of the edit heuristics, relative to a random structural modification, empirical evidence shows that the structural modification specified by the edit heuristic is more likely to preserve target bioactivities associated with typical drug discovery processes. In some embodiments, one or more of the edit heuristics are designed to improve target bioactivities, remove a risk from a molecule, provide insight into whether a particular portion of a molecule is important with respect to target bioactivities, or any combination thereof.

The workflow engine 122 can determine the edit heuristic set 152 that is associated with the search request 128 in any technically feasible fashion. In some embodiments, the workflow engine 122 generates the edit heuristic set 152 based on any number and/or types of commands received in any technically feasible fashion (e.g., from the GUI 106) during the initialization phase. In the same or other embodiments, the workflow engine 122 can add, delete, and/or modify any number of the edit heuristics included in the edit heuristic set 152 based on the search request 128 and/or any number and/or types of commands associated with the search request 128. For instance, in some embodiments, the search request 128 specifies any number and/or types of edit heuristics that are designed to increase the likelihood that applying the edit heuristics to the query molecule specification 150 preserves the target bioactivity associated with the query molecule.

As shown, in some embodiments, the workflow engine 122 inputs the query molecule specification 150 and the edit heuristic set 152 into the derivation engine 160. In response, the derivation engine 160 generates a derivation dataset 162. As shown, in some embodiments, the derivation dataset 162 includes, without limitation, derived molecule specifications 168(1)-168(N) and applied edit lists 164(1)-164(N), where N can be any positive integer.

Each of the derived molecule specifications 168(1)-168(N) represents a different molecule that is derived based on the structure of the query molecule. For explanatory purposes only, the derived molecule specifications 168(1)-168(N) are also referred to herein individually as "the derived molecule specification 168" and collectively as "the derived molecule specifications 168." A molecule that is represented by the derived molecule specification 168 is also referred to herein as a "derived molecule."

The derivation engine 160 can generate the derived molecule specifications 168 based on the query molecule specification 150 and the edit heuristic set 152 in any technically feasible fashion. In some embodiments, the derivation engine 160 applies any number of the edit heuristics included in the edit heuristic set 152 individually and/or in any number of combinations to the query molecule specification 150 to generate the derived molecule specifications 168(1)-168(N).

As persons skilled in the art will recognize, in some embodiments, applying a given edit heuristic to a given molecule specification can produce any number (including zero) of derived molecule specifications 168. For instance, if a given edit heuristic specifies that a substituent is to be removed and a given molecule does not include the substituent, then applying the edit heuristic to the associated molecule specification produces no derived molecule specifications 168. By contrast, if a given edit heuristic specifies a list of substituents that are to be added to a given molecule, then applying the edit heuristic to the associated molecule specification can produce multiple derived molecule specifications 168.

For explanatory purposes only, each of the derived molecules is associated with a number of edits away from the query molecule. The number of edits away that a given derived molecule is from the query molecule refers to the total number of heuristic-based edits that the derivation engine 160 makes, starting with the query molecule specification 150, to generate the derived molecule specification 168 that represents the derived molecule. As referred to herein, a "heuristic-based edit" is an application of one of the edit heuristics to the query molecule specification 150 or one of the derived molecule specifications 168.

For instance, in some embodiments, the derivation engine 160 applies one of the edit heuristics to the query molecule specification 150 to generate the derived molecule specification 168(1) that represents a derived molecule that is one edit away from the query molecule. Subsequently, the derivation engine 160 applies the same or another edit heuristic to the derived molecule specification 168(1) to generate a different one of the derived molecule specifications 168 that represents a derived molecule that is two edits away from the query molecule.

As described in greater detail below in conjunction with FIG. 2, in some embodiments, the derivation engine 160 recursively applies the edit heuristics included in the edit heuristic set 152 to the query molecule specification 150 to generate the derived molecule specifications 168. In some embodiments, during a first iteration, the derivation engine 160 applies each of the edit heuristics to the query molecule specification 150 to generate a first subset of the derived molecule specifications 168. The first subset of the derived molecule specifications 168 represent molecules that are one edit away from the query molecule.

During a second iteration, the derivation engine 160 applies each of the edit heuristics to the first subset of the derived molecule specifications 168 to generate a second subset of the derived molecule specifications 168. The second subset of the derived molecule specifications 168 represent molecules that are two edit away from the query molecule. In some embodiments, the derivation engine 160 continues to apply the edit heuristics to the most recently generated subset of the derived molecule specifications 168 until the derivation engine 160 has exhaustively applied each of the edit heuristics and each possible combination of the edit heuristics to the query molecule specification 150.

As depicted via a dashed box and dashed arrows, in some embodiments, the derivation engine 160 receives an edit limit 154. The edit limit 154 can be any type of constraint that can limit the total number of the derived molecule specifications 168 that the derivation engine 160 generates in any technically feasible fashion. For instance, in some embodiments, the edit limit 154 specifies a maximum number of iterations that the derivation engine 160 can execute. In the same or other embodiments, the edit limit 154 specifies a maximum number of edits that any of the derived molecules can be away from the query molecule. In some embodiments, the derivation engine 160 implements a default value for the edit limit 154.

In some embodiments, as the derivation engine 160 generates the derived molecules specifications 168(1)-168(N), the derivation engine 160 also generates the applied edit lists 164(1)-164(N). The applied edit lists 164(1)-164(N) are also referred to herein individually as "the applied edit list 164" and collectively as "the applied edit lists 164." The applied edit list 164($y$), for an integer y from 1 to N, specifies, without limitation, the edits that the derivation engine 160 applies to the query molecule specification 150 to generate the derived molecule specification 168($y$). The derivation engine 160 can specify the edits included in the applied edit lists 164 at any level of detail and in any technically feasible fashion. In some other embodiments, the derivation engine 160 does not generate the applied edit lists 164, and the applied edit lists 164 are omitted from the derivation dataset 162.

As shown, in some embodiments, the workflow engine 122 inputs the derived molecule specifications 168(1)-168(N) into the molecule mapping engine 134. In response, the molecule mapping engine 134 generates mapped datasets 170(1)-170(N). The mapped datasets 170(1)-170(N) are also referred to herein individually as "the mapped dataset 170" and collectively as "the mapped datasets 170."

Although not shown, the mapped dataset 170($y$), where y in an integer from 1 to N, includes, without limitation, the derived molecule specification 168($y$) and a mapped version of the derived molecule specification 168($y$). As noted previously herein, the mapped version of a molecule specification (including one of the derived molecule specifications 168) is also referred to herein as a "mapped molecule specification."

The molecule mapping engine 134 can generate the mapped versions of the derived molecule specifications 168(1)-168(N) in any technically feasible fashion that is consistent with the mapping operations performed by the catalog mapping engine 130. As shown, in some embodiments, the molecule mapping engine 134 includes, without limitation, the mapping algorithm 132 that is also included in the catalog mapping engine 130. The molecule mapping engine 134 applies the mapping algorithm 132 to each of the derived molecule specifications 168(1)-168(M) to generate the mapped versions of the derived molecule specifications 168(1)-168(M), respectively.

As described previously herein, in some embodiments, the mapping algorithm 132 is a hash function that maps SMILES strings to InChIKeys. In some such embodiments, each of the derived molecule specifications 168 is a SMILES string and each of the mapped versions of the derived molecule specifications 168 is an InChIKey. In the same or other embodiments, each of the mapped datasets 170 includes, without limitation, a SMILES string and an InChIKey that both represent a derived molecule.

As shown, in some embodiments, the workflow engine 122 inputs the mapped datasets 170(1)-170(N) and the mapped catalogs 140(1)-140(M) into the search engines 180(1)-180(M), respectively. In response, the search engines 180(1)-180(M) perform any number and/or type of search operations to generate matching subsets 188(1)-188(M), respectively. The search engines 180(1)-180(M) are different instances of a single search engine 180 (not explicitly shown). For explanatory purposes only, "the search engine 180" as used herein refers to any instance of the search engine 180, irrespective of whether the specific instance is depicted in any of the figures.

In some other embodiments, the molecule exploration application 120 includes less than M instances of the search engine 180, and the workflow engine 122 inputs the mapped datasets 170(1)-170(N) and the mapped catalog 140(1)-140(M) into any number of instances of the search engine 180 sequentially, concurrently, or in any combination thereof. For instance, in some embodiments, the molecule exploration application 120 inputs the mapped datasets 170(1)-170(N) and sequentially inputs the mapped catalog 140(1)-140(M) into a single instance of the search engine 180. In response, the single instance of the search engine 180 sequentially outputs the matching subsets 188(1)-188(M).

The matching subsets 188(1)-188(M) are also referred to herein individually as "the matching subset 188" and collectively as "the matching subsets 188." The matching subset 188($x$), for an integer x from 1 to M, includes, without limitation, each of the derived molecule specifications 168(1)-168(N) that are also included in the molecule catalog 102($x$). As referred to herein, the derived molecule specification 168(*y*), for an integer y from 1 to N, is included in the molecule catalog 102(*x*) if and only if the derived molecule specification 168(*y*) matches one of the available molecule specifications included in the molecule catalog 102(*x*). The matching subset 188(*x*), is therefore the intersection of the set of the derived molecule specifications 168(1)-168(N) and the set of available molecule specifications included in the molecule catalog 102(*x*).

The search engine 180(*x*) can perform any number and/or types of search operations (e.g., comparison operations, etc.) in any technically feasible fashion to determine whether each of the derived molecule specifications 168 matches any of the available molecule specifications included in the molecule catalog 102(*x*). Advantageously, to increase the efficiency of the search operations, the search engine 180(*x*) performs the search operations based, at least in part, on the mapped versions of the derived molecule specifications 168 and the mapped catalog 140(*x*).

As persons skilled in the art will recognize, in some embodiments, the computational complexity of performing search operations based on the mapped versions of the derived molecule specifications 168 and the mapped catalogs 140 is constant with respect to the total number of the available molecules included in the molecule catalogs 102. In the same or other embodiments, because the computational complexity of searching the molecule catalogs 102 for the derived molecule specifications 168 is independent of the total number of the available molecules included in the molecule catalogs 102, all of the available molecules can be searched at an interactive rate. As used herein, "interactive rate" refers to a response rate that does not typically interrupt the flow of interactions between a user and an application as perceived by the user (e.g., a rate less than one second).

As described previously herein, in some embodiments, the mapping algorithm 132 is a hash function, and the search engine 180(*x*) can perform any technically feasible type of hash-based searches to determine whether each of the derived molecule specifications 168(1)-168(N) are included in the molecule catalog 102(*x*). In some such embodiments, the computational complexity of searching the molecule catalogs 102 for the derived molecule specifications 168 is on the order of AAT. As used herein, the symbol A is proportional to the total number of atoms included in the query molecule and the symbol T is the maximum number of edits that any of the derived molecules are away from the query molecule.

In some embodiments, the mapped catalog 140(*x*) is a hash map that stores the available molecule specifications included in the molecule catalog 102(*x*) in any number of buckets based on the mapped versions of the available molecule specifications. To determine whether the derived molecule specification 168(*y*), for an integer y from 1 to N, is included in the molecule catalog 102(*x*), the search engine 180(*x*) implements a hash-based search based on the buckets.

In some embodiments, to intimate a hash-based search, the search engine 180(*x*) identifies a bucket included in the mapped catalog 140(*x*) that is associated with the mapped version of the derived molecule specification 168(*y*). The search engine 180(*x*) then performs a search of the available molecule specifications stored in the identified bucket to determine whether any of the available molecule specifications match the derived molecule specification 168(*y*). If the identified bucket is empty or none of the available molecule specifications stored in the identified bucket match the derived molecule specification 168(*y*), then the search engine 180(*x*) does not add the derived molecule specification 168(*y*) to the matching subset 188(*x*). Otherwise, the search engine 180(*x*) adds the derived molecule specification 168(*y*) to the matching subset 188(*x*).

As shown, in some embodiments, the workflow engine 122 inputs the derivation dataset 162 and the matching subsets 188 into the consolidation engine 190. In response, for each of the derived molecule specifications 168 that is also included in at least one of matching subsets 188, the consolidation engine 190 generates a potential drug candidate dataset (not shown in FIG. 1). Each of the potential drug candidate datasets is associated with a different potential drug candidate. In some embodiments, relative to other available molecules, the potential drug candidates are more likely to be relevant to a drug discovery process associated with the query molecule.

Each of the potential drug candidate datasets includes, without limitation, a potential drug candidate specification (not shown in FIG. 1), a location list (not shown in FIG. 1), and any amount (including none) and/or types of additional data. The potential drug candidate specification is equal to the associated derived molecule specification 168. Each of the location lists specifies, without limitation, at least one of the molecule catalogs 102 that includes the associated potential drug candidate specification. In some embodiments, the consolidation engine 190 generates the location list based on the matching subsets 188 and any number and/or types of preferences that are associated with the molecule catalogs 102.

In some embodiments, the molecule catalogs 102(1)-102(M) are associated with preference rankings of highest to lowest, respectively. If a molecule is included in the molecule catalog 102(1), then the molecule is preferentially obtained from the associated provider. In some such embodiments, for each potential drug candidate dataset, the consolidation engine 190 determines an unordered list based on the matching subsets 188. Each of the unordered lists specifies the subset of the molecule catalogs 102 that include the associated potential drug candidate specification. For each potential drug candidate dataset, the consolidation engine 190 orders the associated unordered list based on the preference rankings to generate the location list.

In the same or other embodiments, each of the potential drug candidate datasets includes a preferred location instead of or in addition to the location list. In some such embodiments, for each potential drug candidate dataset, the consolidation engine 190 specifies, via the preferred location, the molecule catalog 102 having the highest preference ranking of the subset of the molecule catalogs 102 that include the associated potential drug candidate specification.

The consolidation engine 190 generates the search results dataset 198 based on the potential drug candidate datasets and any amount (including none) and/or types of additional data. Although not shown, in some embodiments, the consolidation engine 190 interacts with the workflow engine 122, the derivation engine 160, the search engine 180, or any combination thereof to generate the search results dataset 198. For instance, in some embodiments, the consolidation engine 190 receives the query molecule specification 150 and/or preference rankings associated with the molecule catalogs 102 from the workflow engine 122.

In the same or other embodiments, the consolidation engine 190 interacts with the workflow engine 122 to generate a skeletal structure (not shown in FIG. 1) that graphically represents the query molecule. In the same or other embodiments, for each of the potential drug candidate specifications, the workflow engine 122 interacts with the derivation engine 160 to generate an annotated skeletal structure (not shown in FIG. 1) that graphically represents the potential drug candidate and the structural differences between the potential drug candidate and the query molecule.

As described in greater detail below in conjunction with FIG. 3, in some embodiments, the search results dataset 198 includes, without limitation, a search report, a query dataset, and a search summary. In some embodiments, the search report includes, without limitation, the potential drug candidate datasets. In the same or other embodiments, the query dataset includes, without limitation, any amount and/or types of data associated with the query molecule. In some embodiments, the search summary includes, without limitation, any amount and/or types of data (e.g., statistics) associated with the search operations performed on the molecule catalogs 102 via the mapped catalog 140.

As shown, in some embodiments, the workflow engine 122 displays any portion (including all) of the search results dataset 198 via the GUI 106. In the same or other embodiments, the workflow engine 122 provides any portion of the search results dataset 198 to any number of users and/or any number and/or types of software application instead of or in additional to displaying any portion of the search results dataset 198 via the GUI 106. In the same or other embodiments, the GUI 106 is omitted from the system 100 and the workflow engine 122 can acquire input data and provide output data in any technically feasible fashion.

Advantageously, by preferentially evaluating the potential drug candidates when determining additional drug development candidates, the overall efficiency of the drug discovery process can be increased. In particular, because the edit heuristics set 152 can be tailored for a given drug discovery process, the relevance of the potential drug candidates to drug discovery processes can be increased relative to conventional potential drug candidates that are determined based on similarity metrics. As a result, in some embodiments, the amounts of time and resources that are wasted evaluating molecules that do not have the target bioactivity when determining additional drug development candidates can be reduced.

Note that the techniques described herein are illustrative rather than restrictive and may be altered without departing from the broader spirit and scope of the invention. Many modifications and variations on the functionality provided by the molecule exploration application 120, the workflow engine 122, the catalog mapping engine 130, the derivation engine 160, the molecule mapping engine 134, the search engine 180, and the consolidation engine 190 will be apparent to those of ordinary skill in the art without departing from the scope and spirit of the described embodiments. For instance, in some embodiments, the functionality provided by the molecule exploration application 120 as described herein is partitioned into an initialization application (not shown) and a search application (not shown) that are stored in different memories 116 and execute on different processors 112. In some embodiments, the connection topology between the various components in FIG. 1 may be modified as desired.

Applying Edit Heuristics to Query Molecule Specification

Figure 2:
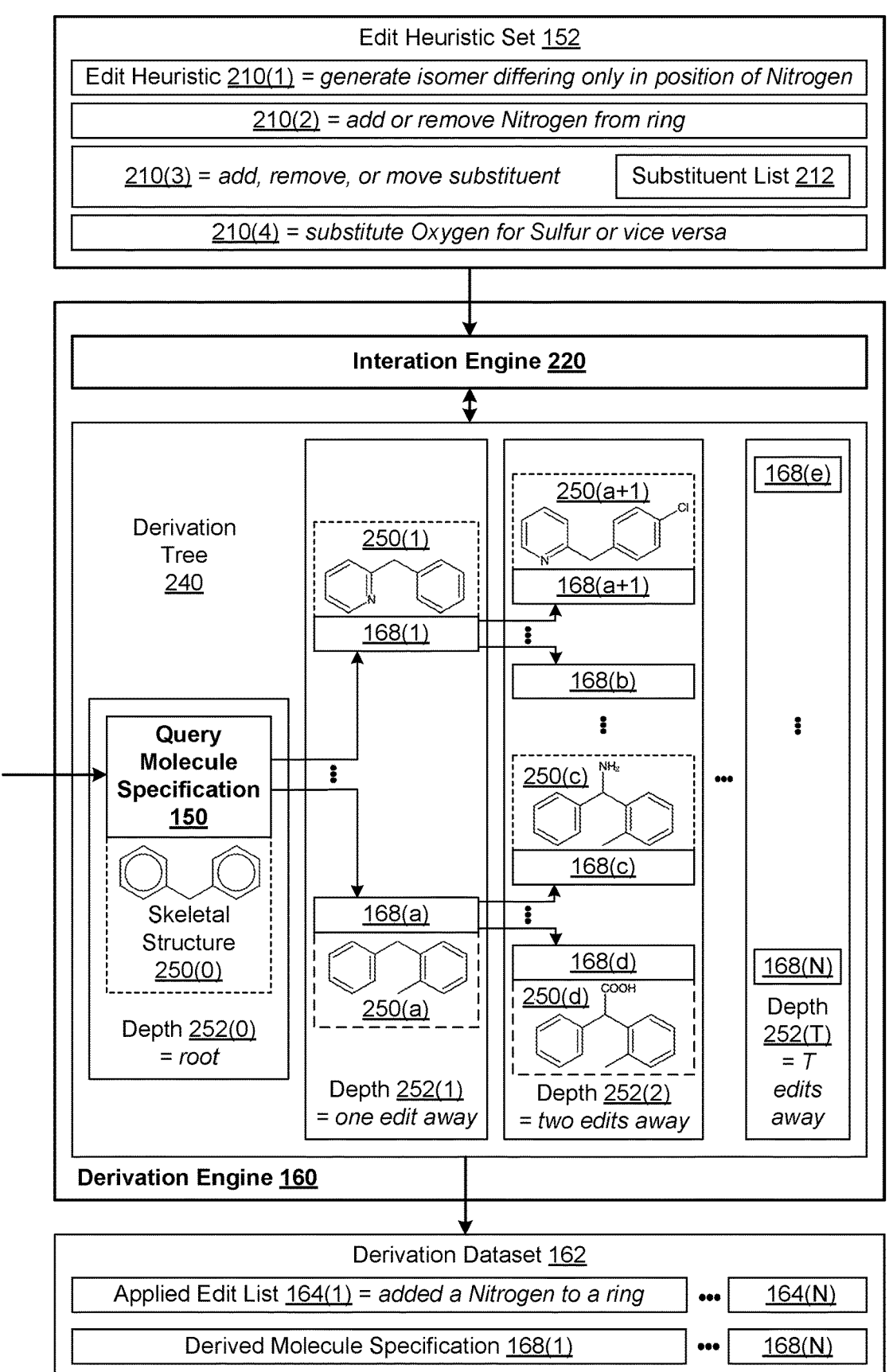
FIG. 2 is a more detailed illustration of the derivation engine of FIG. 1, according to various embodiments.

FIG. 2 is a more detailed illustration of the derivation engine 160 of FIG. 1, according to various embodiments. As shown, in some embodiments, the derivation engine 160 generates the derivation dataset 162 based on the query molecule specification 150 and the edit heuristic set 152 that includes, without limitation, the edit heuristics 210(1)-210(4). The edit heuristics 210(1)-210(4) are also referred to herein individually as "the edit heuristic 210" and collectively as "the edit heuristics 210." In other embodiments, the edit heuristic set 152 can include any number and/or types of edit heuristics 210.

As described previously herein in conjunction with FIG. 1, each of the edit heuristics 210 specifies a different type of modification to the structure of an existing molecule. For explanatory purposes only, exemplary functions associated with the edit heuristics 210(1)-210(4) are depicted in italics. As shown, the function of the edit heuristic 210(1) is to generate an isomer differing only in the position of a Nitrogen. The function of the edit heuristic 210(2) is to add or remove a Nitrogen from a ring. As shown, the edit heuristic 210(3) includes, without limitation, a substituent list 212. The function of the edit heuristic 210(3) is to add, remove, or move (e.g., reposition) one of any number of substituents included in the substituent list 212. Some examples of substituents include, without limitation, the amino group ("NH$_2$"), the carboxyl group ("COOH"), etc. The function of the edit heuristic 210(4) is to substitute an Oxygen for a Sulfur or vice versa.

As shown, the derivation engine 160 includes, without limitation, an iteration engine 220 that incrementally generates a derivation tree 240. For explanatory purposes only, the depiction of the derivation tree 240 is annotated with skeletal structures 250(0)-250(N) via dashed boxes. The skeletal structures 250(0)-250(N) are also referred to herein individually as "the skeletal structure 250" and collectively as "the skeletal structures 250." Each of the skeletal structures 250 is a 2D representation of an associated molecule that depicts, without limitation, how the atoms of the molecule can be arranged in 3D space. The skeletal structure 250(0) graphically depicts the query molecule represented by the query molecule specification 150. The skeletal structures 250(1)-250(N) graphically depict the derived molecules represented by the derived molecule specifications 168(1)-168(N), respectively.

In the embodiment depicted in FIG. 2, the skeletal structures 250 are illustrative only and are not included in the derivation tree 240 generated by the iteration engine 220. In some other embodiments, the derivation engine 160 and/or the iteration engine 220 can acquire (e.g., receive, generate, etc.) the skeletal structures 250(0)-250(N) in any technically feasible fashion. In some such embodiments, the derivation engine 160 and/or the iteration engine 220 adds the skeletal structures 250 to the derivation tree 240 and/or the derivation dataset 162. In the same or other embodiments, the derivation engine 160, the iteration engine 220, the workflow engine 122, or any combination thereof can display any portion of the derivation tree 240 and/or any portion of the derivation dataset 162 via the GUI 106.

In some embodiments, the iteration engine 220 generates the derivation tree 240 that includes, without limitation, depths 242(0)-242(T), where T can be any positive integer. The depths 242(0)-242(T) are also referred to herein individually as "the depth 242" and collectively as "the depths 242." For explanatory purposes, and as described in detail below, T is an integer that is greater than 3 in the embodiment depicted in FIG. 2.

When the derivation engine 160 receives the query molecule specification 150, the iteration engine 220 generates an initial version of the derivation tree 240 that includes, without limitation, the depth 252(0) that corresponds to the root of the derivation tree 240. The iteration engine 220 adds the query molecule specification 150 to the derivation tree

240 at the depth 252(0). As a result, the depth 252(0) includes, without limitation, the query molecule specification 150. For illustrative purposes only, the skeletal structure 250(0) of an exemplary query molecule represented by the query molecule specification 150 is depicted via a dashed box.

During a first iteration, the iteration engine 220 individually applies each of the edit heuristics 210 included in the edit heuristic set 152 to the query molecule specification 150. As described previously herein in conjunction with FIG. 1, in some embodiments, applying each of the edit heuristics 210 to the query molecule specification 150 can produce any number (including zero) of the derived molecule specifications 168.

As shown, during the first iteration, the iteration engine 220 generates the derived molecule specifications 168(1)-168(a), where a can be any positive integer. The iteration engine 220 adds the derived molecule specifications 168(1)-168(a) to the derivation tree 240 at the depth 252(1) that is associated with derived molecules that are 1 edit away from the query molecule. For illustrative purposes only, the skeletal structures 250(1)-250(a) of the derived molecules represented by the derived molecule specifications 168(1)-168(a), respectively, are depicted via dashed boxes.

During a second iteration, the iteration engine 220 individually applies each of the edit heuristics 210 to each of the derived molecule specifications 168(1)-168(a) that are at the depth 252(1). More precisely, as shown, the iteration engine 220 individually applies each of the edit heuristics 210 to the derived molecule specification 168(1) to generate the derived molecule specifications 168(a+1)-168(b), where b can be any integer that is greater than a. Although not shown, the iteration engine 220 individually applies each of the edit heuristics 210 to each of the derived molecule specifications 168(2)-168(a−1) to generates the derived molecule specifications 168(b+1)-168(c−1), where c can be any integer that is greater than b. As shown, the iteration engine 220 individually applies each of the edit heuristics 210 to the derived molecule specification 168(a) to generate the derived molecule specifications 168(c)-168(d), where d can be any integer that is greater than c.

The iteration engine 220 adds the derived molecule specifications 168(a+1)-168(d) to the derivation tree 240 at the depth 252(2) that is associated with derived molecules that are 2 edits away from the query molecule. For illustrative purposes only, the skeletal structures 250(a+1), 250(c), and 250(d) of the derived molecules represented by the derived molecule specifications 168(a+1), 168(c), and 168(d), respectively, are depicted via dashed boxes.

Subsequently, although not explicitly shown, the iteration engine 220 iteratively generates the derived molecule specifications 168(d+1)-168(e−1), where e is any integer greater than d, that are distributed across the depths 252(3)-252(T−1), where T is any positive integer that is greater than 3. The depths 252(3)-252(T−1) are associated with derived molecules that are 3-(T−1), respectively, edits away from the query molecule. In the embodiment depicted in FIG. 2, the iteration engine 220 generates the derived molecule specifications 168 that are at the depths 252(3)-252(T−1) based on the derived molecule specifications that are at the depths 252(2)-252(T−2), respectively.

The iteration engine 220 generates the derived molecule specifications 168(e)-168(N), where N is any integer greater than e, based on the derived molecule specifications 168 that are at the depth 252(T−1). The iteration engine 220 adds the derived molecule specifications 168(e)-168(N), to the derivation tree 240 at the depth 252(T) that is associated with derived molecules that are T edits away from the query molecule. The iteration engine 220 then determines that the iteration engine 220 has exhaustively applied each of the edit heuristics 210 and each possible combination of the edit heuristics 210 to the query molecule specification 150 and, as a result, ceases to iterate.

After the iteration engine 220 ceases to iterate, the derivation tree 240 includes, without limitation, the query molecule specification 150 at the depth 252(0), and the derived molecule specifications 168(1)-168(N) distributed across the depths 252(1)-252(T). The derivation engine 160 generates the derivation dataset 162 based on the derivation tree 240. As described previously herein, in some embodiments, the derivation dataset 162 includes, without limitation, the derived molecule specifications 168(1)-168(N) and the applied edit lists 164(1)-164(N).

As described previously herein in conjunction with FIG. 2, the applied edit list 164(y), for an integer y from 1 to N, specifies, without limitation, the edits that the iteration engine 220 applies to the query molecule specification 150 to generate the derived molecule specifications 168(y). The derivation engine 160 can specify the edits included in the applied edit lists 164 at any level of detail and in any technically feasible fashion. As shown in italics for explanatory purpose only, in some embodiments, the derivation engine 160 sets the applied edit list 164(1) equal to "added a Nitrogen to a ring."

FIG. 3 is a more detailed illustration of the search results dataset 198 of FIG. 1, according to various embodiments. As described previously herein in conjunction with FIG. 1, the consolidation engine 190 can generate the search results dataset 198 in any technically feasible fashion. For explanatory purposes only, FIG. 3 depicts an example of the search results dataset 198 that the consolidation engine 190 generates based, at least in part, on the example of the derivation dataset 162 depicted in FIG. 2. In some other embodiments, the search results dataset 198 can specific any number of potential drug candidates and any amount and/or types of associated data in any technically feasible fashion.

As shown, in some embodiments, the search results dataset 198 includes, without limitation, a query dataset 302, a search summary 310, and a search report 380. The query dataset 302 describes the query molecule and includes, without limitation, the query molecule specification 150 and the skeletal structure 250(0). Referring back to FIG. 2, the skeletal structure 250(0) is a 2D representation of the query molecule that depicts, without limitation, how the atoms of the query molecule can be arranged in 3D space.

The search summary 310 describes a 2D table that is associated with the search operations that the search engine 180 performs on the molecule catalogs 102 via the mapped catalogs 140. As shown, the search summary includes, without limitation, rows 312(1)-312(M), columns 314(1)-314(T), and match counts 320(1, 1)-320(M, T). The rows 312(1)-312(M) correspond to the molecule catalogs 102(1)-102(M), respectively, and are also referred to herein individually as "the row 312" and collectively as "the rows 312." The columns 314(1)-314(T) correspond to the depths 252(1)-252(T), respectively, and are also referred to herein individually as "the column 314" and collectively as "the column 314."

The match counts 320(1, 1)-320(M, T) are also referred to herein individually as "the match count 320" and collectively as "the match counts 320." Referring back to FIGS. 1 and 2, the match count 320(i, j), where is an integer between 1 and M and j is an integer between 1 and T, is the total number of the derived molecule specifications 168 associated with the depth $252(j)$ that are included in the matching subset $188(i)$. Consequently, the match count $320(i, j)$ specifies the total number of the derived molecules that are j edits away from the query molecule that are specified in the molecule catalog $102(i)$.

For explanatory purposes only, some exemplary values for the match counts $320$ are depicted in italics. As shown, the match count $320(1, 1)$ is 4, indicating that the molecule catalog $102(1)$ includes representations of 4 of the derived molecules that are one edit away from the query molecule. The match count $320(2, 1)$ is 17, indicating that the molecule catalog $102(2)$ includes representations of 17 of the derived molecules that are one edit away from the query molecule. The match count $320(M, 1)$ is 0, indicating that the molecule catalog $102(M)$ includes representations of none of the derived molecules that are one edit away from the query molecule.

As also shown, the match count $320(1, T)$ is 10, indicating that the molecule catalog $102(1)$ includes representations of 10 of the derived molecules that are T edits away from the query molecule. The match count $320(2, 1)$ is 167, indicating that the molecule catalog $102(2)$ includes representations of 167 of the derived molecules that are T edits away from the query molecule. The match count $320(M, T)$ is 2, indicating that the molecule catalog $102(M)$ includes representations of 2 of the derived molecules that are T edits away from the query molecule.

As shown, in some embodiments, the search report $380$ includes, without limitation, potential drug candidate datasets $390(1)-390(P)$, where P is an integer that is less than or equal to N (the total number of the derived molecule specifications $168$). For explanatory purposes only, the potential drug candidate datasets $390(1)-390(P)$ are also referred to herein individually as "the potential drug candidate dataset $390$" and collectively as "the potential drug candidate datasets $390$." Each of the potential drug candidate datasets $390$ describes a different potential drug candidate.

As shown, the potential drug candidate dataset $390(1)$ includes, without limitation, a potential drug candidate specification $392(1)$, a location list $394(1)$, an annotated skeletal structure $396(1)$, and a modification level $398(1)$. As also shown, the potential drug candidate dataset $390(P)$ includes, without limitation, a potential drug candidate specification $392(P)$, a location list $394(P)$, an annotated skeletal structure $396(P)$, and a modification level $398(P)$. Although not shown explicitly, the potential drug candidate datasets $390(k)$, where k is an integer between 2 and P−1, includes, without limitation, a potential drug candidate specification $392(k)$, a location list $394(k)$, an annotated skeletal structure $396(k)$, and a modification level $398(k)$.

Each of the potential drug candidate specifications $392(1)-392(P)$ is equal to a different one of the derived molecule specifications $168$ that is included in at least one of the molecule catalogs $102$. Each of the location lists $394(1)-394(P)$ specifies, without limitation, the subset of the molecule catalogs $102$ that include the potential drug candidate specifications $392(1)-393(P)$, respectively. In some embodiments, each of the location lists $394(1)-394(P)$ is ordered based on preference rankings associated with the molecule catalogs $102$.

The annotated skeletal structures $396(1)-396(P)$ are the skeletal structures $250$ representing the associated potential molecules that are annotated in any technically feasible fashion (e.g., via a coloring scheme) to graphically depict the structural differences between the associated potential drug candidate and the query molecule. The consolidation engine $190$ can acquire the annotated skeletal structures $396(1)-396(P)$ in any technically feasible fashion. In some embodiments, the workflow engine $122$, the derivation engine $160$, the consolidation engine $190$, or any combination thereof can generate the annotated skeletal structures $396(1)-396(P)$.

The modification levels $398(1)-398(P)$ specify the total number of the edit heuristics $210$ that the derivation engine $160$ applied to the query molecule specification $150$ to generate the potential drug candidate specifications $392(1)-392(P)$, respectively. Referring back to FIG. $2$, in some embodiments, each of the modification levels $398(1)-398(P)$ is a different depth $252$ and therefore indicates a total number of edits away from the query molecule.

For explanatory purposes only, some exemplary values for the potential drug candidate datasets $390(1)$ and $390(P)$ are depicted in italics. As shown, the potential drug candidate specification $392(1)$ is the derived molecule specification $168(3)$ (not explicitly depicted). The location list $394(1)$ indicates that the potential drug candidate specification $392(1)$ is included in the molecule catalog $102(2)$. The modification level $398(1)$ indicates the potential drug candidate described by the potential drug candidate specification $392(1)$ is one edit away from the query molecule.

In some embodiments, the potential drug candidate specification $392(P)$ is the derived molecule specification $168(e)$ (depicted in FIG. $2$). The location list $394(P)$ indicates that the potential drug candidate specification $392(P)$ is included in the molecule catalogs $102(1)$ and $102(M)$. The modification level $398(1)$ indicates the potential drug candidate described by the potential drug candidate specification $392(1)$ is T edits away from the query molecule.

FIG. $4$ is a flow diagram of method steps for determining potential drug candidates during drug discovery processes, according to various embodiments. Although the method steps are described with reference to the systems of FIGS. $1-3$, persons skilled in the art will understand that any system configured to implement the method steps, in any order, falls within the scope of the present invention.

As shown, a method $400$ begins a step $402$, where any number of instances of the catalog mapping engine $130$ generate the mapped catalogs $140(1)-140(M)$ based on the molecule catalogs $102(1)-102(M)$ and the mapping algorithm $132$. The workflow engine $122$ then waits for the search request $128$. In some embodiments, the workflow engine $122$ stores any number of the mapped catalogs $140(1)-140(M)$ in any memory that is accessible to the molecule exploration application $120$.

At step $404$, the workflow engine $122$ determines the query molecule specification $150$ and the edit heuristic set $152$ associated with the search request $128$. At step $406$, the derivation engine $160$ computes the derived molecule specifications $168(1)-168(N)$ and optionally the applied edit lists $164(1)-164(N)$ based on the query molecule specification $150$ and the edit heuristic set $152$.

At step $408$, the molecule mapping engine $134$ computes mapped versions of the derived molecule specifications $168(1)-168(N)$ based on the mapping algorithm $132$. At step $410$, any number of instances of the search engine $180$ search each of the molecule catalogs $102(1)-102(M)$ for each of the derived molecule specifications $168(1)-168(N)$ via the mapped catalogs $140(1)-140(M)$ and the mapped versions of the derived molecule specifications $168(1)-168(N)$ to generate the matching subsets $188(1)-188(M)$.

At step $412$, the consolidation engine $190$ generates the potential drug candidate datasets $390$ based on the matching subsets $188$. At step $414$, the consolidation engine $190$ generates the search results dataset 198 based on the potential drug candidate datasets 390 and optionally any number of the query molecule specification 150, the derived molecule specifications 168, and the applied edit lists 164.

At step 416, the workflow engine 122 stores and/or provides any portion of the search results dataset 198 to any number of users and/or types of software applications for use in determining additional drug development candidates. At step 418, the workflow engine 122 determines whether the workflow engine 122 has received a new search request 128. If, at step 418, the workflow engine 122 determines that the workflow engine 122 has not received a new search request 128, then the method 400 terminates.

If, however, at step 418, the workflow engine 122 determines that the workflow engine 122 has received a new search request 128, then the method 400 returns to step 404, where the workflow engine 122 determines the query molecule specification 150 and the edit heuristic set 152 associated with the search request 128. The method 400 continues to cycle through steps 404-418, generating new search results datasets 198 until the workflow engine 122 determines, at step 418, that the workflow engine 122 has not received a new search request 128. The method 400 then terminates.

In sum, the disclosed techniques can be used to derive potential drug candidates for a drug discovery process based on a query molecule, edit heuristics that are tailored for drug discovery processes, and any number of molecule catalogs. In some embodiments, a molecule exploration application includes, without limitation, a workflow engine, a catalog mapping engine, a derivation engine, a molecule mapping engine, a search engine, and a consolidation engine.

During an initialization phase, the workflow engine inputs the molecule catalogs into any number of instances of the catalog mapping engine to generate mapped catalogs. Each of the molecule catalogs includes, without limitation, any number of available molecule specifications, where each of the available molecule specifications represents a different existing molecule. Each of the mapped catalogs includes, without limitation, mapped versions of the available molecule specifications included in the associated molecule catalog. To generate the mapped catalog corresponding to a given molecule catalog, the catalog mapping engine applies a mapping algorithm (e.g., a hash function) to each of the available molecule specifications included in the molecule catalog.

Subsequently, during a search phase, the workflow engine receives any number search requests, where each search request is associated with a query molecule. In some embodiments, the query molecule is a drug development candidate of interest in a drug discovery process. In response to a given search request, the workflow engine determines a query molecule specification and an edit heuristic set. The query molecule specification represents the query molecule associated with the search request.

The edit heuristic set includes, without limitation, any number and/or types of edit heuristics that each specifies a different type of modification to the structure of an existing molecule. The edit heuristics are typically designed to have some relevance to one or more drug discovery processes. In particular, for each of at least one of the edit heuristics, relative to a random structural modification, empirical evidence shows that the structural modification specified by the edit heuristic is more likely to preserve target bioactivities associated with typical drug discovery processes.

The derivation engine iteratively applies the edit heuristics included in the edit heuristic set to the associated query molecule specification to generate derived molecule specifications corresponding to all possible combinations of the edit heuristics. The molecule mapping engine then applies the mapping algorithm to each of the derived molecule specifications to generate mapped versions of the derived molecule specifications. Importantly, the molecule mapping engine and the catalog mapping engine implement the same mapping algorithm.

The search engine performs any number and/or type of search operations on each of the molecule catalogs based on the associated mapped catalog and the mapped versions of the derived molecule specifications to generate an associated matching subset of the derived molecule specifications. The matching subset associated with a given molecule catalog specifies, without limitation, the derived molecule specifications that match available molecule specifications included in the molecule catalog.

Based on the matching subsets, the workflow engine generates a search result dataset that specifies, without limitation, any number of potential drug candidate specifications and associated location lists. Each of the potential drug candidate specifications is a different derived molecule specification that matches at least one of the available molecule specifications. For each of the potential drug candidate specifications, the associated location list specifies at least one of the molecule catalogs that includes the potential drug candidate specification. The workflow engine then provides any portion of the search result dataset to any number of users (e.g., via a GUI) and/or transmits any portion of the search result dataset to any number of other software applications.

At least one technical advantage of the disclosed techniques relative to the prior art is that the molecule exploration application can be used to more efficiently determine additional drug development candidates during a drug discovery process. In particular, because the edit heuristics are tailored for drug discovery processes, the likelihood that each of the derived molecule specifications represents a molecule that has the target bioactivity is increased. Consequently, the proportion of the potential drug candidates that ultimately are determined to be additional drug development candidates is typically increased relative to prior art approaches. Furthermore, unlike prior art techniques, because the computational complexity of the operations performed by the search engine remains constant regardless of the total number of molecules being searched, the amounts of time and computational resources required to comprehensively search the molecule catalogs can be reduced. Notably, with the disclosed techniques, all of the available molecules can be searched at a given interactive rate. These technical advantages provide one or more technological improvements over prior art approaches.

1. In some embodiments, a computer-implemented method for determining one or more potential drug candidates during a drug discovery process comprises generating a plurality of derived molecule specifications based on a query molecule specification and a plurality of edit heuristics, performing, via a mapping algorithm, one or more mapping operations on the plurality of derived molecule specifications to generate a plurality of mapped molecule specifications, and performing one or more search operations on a mapped catalog of molecules based on the plurality of mapped molecule specifications to determine the one or more potential drug candidates.

2. The computer-implemented method of clause 1, further comprising performing, via the mapping algorithm, one or more mapping operations on a plurality of molecule specifications associated with a catalog of molecules to generate the mapped catalog of molecules.

3. The computer-implemented method of clauses 1 or 2, wherein generating the plurality of derived molecule specifications comprises recursively applying the plurality of edit heuristics to the query molecule specification to generate a derivation tree that includes the plurality of derived molecule specifications.

4. The computer-implemented method of any of clauses 1-3, wherein generating the plurality of derived molecule specifications comprises applying a first edit heuristic included in the plurality of edit heuristics to the query molecule specification to generate a first derived molecule specification, and applying a second edit heuristic included in the plurality of edit heuristics to the first derived molecule specification to generate a second derived molecule specification.

5. The computer-implemented method of any of clauses 1-4, wherein the plurality of edit heuristics includes at least one edit heuristic that, when applied to the query molecule specification, adds a Nitrogen or a substituent to the query molecule specification, removes a Nitrogen or a substituent from the query molecule specification, or repositions a substituent included in the query molecule specification to generate a derived molecule specification.

6. The computer-implemented method of any of clauses 1-5, wherein the plurality of edit heuristics includes at least one edit heuristic that, when applied to the query molecule specification, repositions a Nitrogen included in the query molecule specification to generate a derived molecule specification that represents an isomer of a query molecule corresponding to the query molecule specification.

7. The computer-implemented method of any of clauses 1-6, wherein the mapping algorithm comprises a hash function, and the mapped catalog of molecules comprises a hash map.

8. The computer-implemented method of any of clauses 1-7, wherein performing the one or more search operations comprises performing a hash-based search on the mapped catalog of molecules based on a first mapped molecule specification included in the plurality of mapped molecule specifications to determine that a first derived molecule specification included in the plurality of derived molecule specifications matches a first molecule specification included in the mapped catalog of molecules.

9. The computer-implemented method of any of clauses 1-8, further comprising performing another hash-based search on another mapped catalog of molecules to determine that the first derived molecule specification matches a second molecule specification included in the another mapped catalog of molecules, determining that a first catalog of molecules corresponding to the mapped catalog of molecules has a first preference ranking that is lower than a second catalog of molecules corresponding to the another mapped catalog of molecules, and displaying on a computing device, via a graphical user interface, that a first derived molecule corresponding to the first derived molecule specification is a first potential drug candidate and is located in the second catalog of molecules.

10. The computer-implemented method of any of clauses 1-9, wherein the query molecule specification represents a drug development candidate of interest associated with the drug discovery process.

11. In some embodiments, one or more non-transitory computer readable media include instructions that, when executed by one or more processors, cause the one or more processors to determine one or more potential drug candidates during a drug discovery process by performing the steps of generating a plurality of derived molecule specifications based on a query molecule specification and a plurality of edit heuristics, performing, via a mapping algorithm, one or more mapping operations on the plurality of derived molecule specifications to generate a plurality of mapped molecule specifications, and searching a catalog of molecules for each derived molecule specification included in the plurality of derived molecule specifications based on the plurality of mapped molecule specifications and a mapped catalog of molecules to determine the one or more potential drug candidates.

12. The one or more non-transitory computer readable media of clause 11, further comprising performing, via the mapping algorithm, one or more mapping operations on a plurality of molecule specifications associated with a catalog of molecules to generate the mapped catalog of molecules.

13. The one or more non-transitory computer readable media of clauses 11 or 12, wherein generating the plurality of derived molecule specifications comprises recursively applying the plurality of edit heuristics to the query molecule specification to generate a derivation tree that includes the plurality of derived molecule specifications.

14. The one or more non-transitory computer readable media of any of clauses 11-13, wherein generating the plurality of derived molecule specifications comprises applying a first edit heuristic included in the plurality of edit heuristics to the query molecule specification to generate a first derived molecule specification, and applying a second edit heuristic included in the plurality of edit heuristics to the query molecule specification to generate a second derived molecule specification.

15. The one or more non-transitory computer readable media of any of clauses 11-14, wherein the plurality of edit heuristics includes at least one edit heuristic that, when applied to the query molecule specification, adds a Nitrogen or a substituent to the query molecule specification, removes a Nitrogen or a substituent from the query molecule specification, or repositions a substituent included in the query molecule specification to generate a derived molecule specification.

16. The one or more non-transitory computer readable media of any of clauses 11-15, wherein the plurality of edit heuristics includes at least one edit heuristic that, when applied to the query molecule specification, replaces an Oxygen included in the query molecule specification with a Sulfur or replaces a Sulfur included in the query molecule specification with an Oxygen.

17. The one or more non-transitory computer readable media of any of clauses 11-16, wherein the one or more mapping operations map the plurality of derived molecule specifications to a vector space to generate the plurality of mapped molecule specifications.

18. The one or more non-transitory computer readable media of any of clauses 11-17, wherein searching the catalog of molecules comprises performing a hash-based search on the mapped catalog of molecules based on a first mapped molecule specification included in the plurality of mapped molecule specifications to determine that a first derived molecule specification include in the plurality of derived molecule specifications matches a first molecule specification included in the mapped catalog of molecules.

19. The one or more non-transitory computer readable media of any of clauses 11-18, wherein the query molecule specification represents a drug development candidate of interest associated with the drug discovery process.

20. In some embodiments, a system comprises one or more memories storing instructions and one or more processors coupled to the one or more memories that, when executing the instructions, perform the steps of generating a plurality of derived molecule specifications based on a query molecule specification and a plurality of edit heuristics, applying a mapping algorithm to each derived molecule specification included in the plurality of derived molecule specifications to generate a plurality of mapped molecule specifications, and performing one or more search operations on a mapped catalog of molecules based on the plurality of mapped molecule specifications to determine one or more potential drug candidates.

Any and all combinations of any of the claim elements recited in any of the claims and/or any elements described in this application, in any fashion, fall within the contemplated scope of the embodiments and protection.

The descriptions of the various embodiments have been presented for purposes of illustration but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "module," a "system," or a "computer." In addition, any hardware and/or software technique, process, function, component, engine, module, or system described in the present disclosure may be implemented as a circuit or set of circuits.

As previously set forth herein, aspects of the present disclosure may take the form of a computer program product embodied in one or more computer readable media having computer readable program codec embodied thereon. Any combination of one or more computer readable media may be utilized. Each computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory, a read-only memory, an erasable programmable read-only memory, or a Flash memory), an optical fiber, a portable compact disc read-only memory, an optical storage device, a magnetic storage device, or any suitable combination of the foregoing. In the context of this document, a computer readable storage medium may be any tangible medium that can contain or store a program for use by or in connection with an instruction execution system, apparatus, or device.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine. The instructions, when executed via the processor of the computer or other programmable data processing apparatus, enable the implementation of the functions/acts specified in the flowchart and/or block diagram block or blocks. Such processors may be, without limitation, general purpose processors, special-purpose processors, application-specific processors, or field-programmable gate arrays.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the preceding is directed to embodiments of the present disclosure, other and further embodiments of the disclosure may be devised without departing from the basic scope thereof, and the scope thereof is determined by the claims that follow.

What is claimed is:

1. A computer-implemented method for determining one or more potential drug candidates during a drug discovery process, the method comprising:

generating a plurality of likelihoods by determining, for each more edit heuristic included in a plurality of edit heuristics, a likelihood that a target bioactivity associated with a query molecule specification is preserved when the edit heuristic is applied to the query molecule specification, wherein each edit heuristic included in the plurality of edit heuristics specifies a different type of modification to a structure of an existing molecule;

generating a subset of the plurality of edit heuristics based on the plurality of likelihoods;

applying the subset of the plurality of edit heuristics to the query molecule specification to generate a plurality of derived molecule specifications;

performing one or more mapping operations on the plurality of derived molecule specifications to generate a plurality of mapped molecule specifications that are compressed digital representations of the plurality of derived molecule specifications;

performing one or more hash-based search operations on a mapped catalog of available molecules that can be acquired based on the plurality of mapped molecule specifications to determine the one or more potential drug candidates; and causing one or more search results that include the one or more potential drug candidates to be outputted.

2. The computer-implemented method of claim 1, further comprising performing one or more mapping operations on a plurality of molecule specifications associated with a catalog of molecules to generate the mapped catalog of molecules.

3. The computer-implemented method of claim 1, wherein generating the plurality of derived molecule specifications comprises recursively applying the subset of the plurality of edit heuristics to the query molecule specification to generate a derivation tree that includes the plurality of derived molecule specifications.

4. The computer-implemented method of claim 1, wherein generating the plurality of derived molecule specifications comprises:

applying a first edit heuristic included in the subset of the plurality of edit heuristics to the query molecule specification to generate a first derived molecule specification; and applying a second edit heuristic included in the subset of the plurality of edit heuristics to the first derived molecule specification to generate a second derived molecule specification.

5. The computer-implemented method of claim 1, wherein the plurality of edit heuristics includes at least one edit heuristic that, when applied to the query molecule specification, adds a Nitrogen or a substituent to the query molecule specification, removes a Nitrogen or a substituent from the query molecule specification, or repositions a substituent included in the query molecule specification to generate a derived molecule specification.

6. The computer-implemented method of claim 1, wherein the plurality of edit heuristics includes at least one edit heuristic that, when applied to the query molecule specification, repositions a Nitrogen included in the query molecule specification to generate a derived molecule specification that represents an isomer of a query molecule corresponding to the query molecule specification.

7. The computer-implemented method of claim 1, wherein the one or more mapping operations comprise applying a hash function to the plurality of derived molecule specifications to generate a plurality of array indices included in the plurality of mapped molecule specifications.

8. The computer-implemented method of claim 1, wherein performing the one or more hash-based search operations comprises performing a hash-based search on the mapped catalog of molecules based on a first mapped molecule specification included in the plurality of mapped molecule specifications to determine that a first derived molecule specification included in the plurality of derived molecule specifications matches a first molecule specification included in the mapped catalog of molecules.

9. The computer-implemented method of claim 8, further comprising:

performing another hash-based search on another mapped catalog of molecules to determine that the first derived molecule specification matches a second molecule specification included in the another mapped catalog of molecules;

determining that a first catalog of molecules corresponding to the mapped catalog of molecules has a first preference ranking that is lower than a second catalog of molecules corresponding to the another mapped catalog of molecules; and displaying on a computing device, via a graphical user interface, that a first derived molecule specification corresponding to the first derived molecule specification is a first potential drug candidate and is located in the second catalog of molecules.

10. The computer-implemented method of claim 1, wherein the query molecule specification represents a drug development candidate of interest associated with the drug discovery process.

11. One or more non-transitory computer readable media including instructions that, when executed by one or more processors, cause the one or more processors to determine one or more potential drug candidates during a drug discovery process by performing the steps of:

generating a plurality of likelihoods by determining, for each edit heuristic included in a plurality of edit heuristics, a likelihood that a target bioactivity associated with a query molecule specification is preserved when the edit heuristic is applied to the query molecule specification, wherein each edit heuristic included in the plurality of edit heuristics specifies a different type of modification to a structure of an existing molecule;

generating a subset of the plurality of edit heuristics based on the plurality of likelihoods;

applying the subset of the plurality of edit heuristics to the query molecule specification to generate a plurality of derived molecule specifications;

performing one or more mapping operations on the plurality of derived molecule specifications to generate a plurality of mapped molecule specifications that are compressed digital representations of the plurality of derived molecule specifications;

performing one or more hash-based search operations on a mapped catalog of available molecules that can be acquired based on the plurality of mapped molecule specifications to determine the one or more potential drug candidates; and causing one or more search results that include the one or more potential drug candidates to be outputted.

12. The one or more non-transitory computer readable media of claim 11, further comprising performing one or more mapping operations on a plurality of molecule specifications associated with a catalog of molecules to generate the mapped catalog of molecules.

13. The one or more non-transitory computer readable media of claim 11, wherein generating the plurality of derived molecule specifications comprises recursively applying the subset of the plurality of edit heuristics to the query molecule specification to generate a derivation tree that includes the plurality of derived molecule specifications.

14. The one or more non-transitory computer readable media of claim 11, wherein generating the plurality of derived molecule specifications comprises:

applying a first edit heuristic included in the subset of the plurality of edit heuristics to the query molecule specification to generate a first derived molecule specification; and applying a second edit heuristic included in the subset of the plurality of edit heuristics to the query molecule specification to generate a second derived molecule specification.

15. The one or more non-transitory computer readable media of claim 11, wherein the plurality of edit heuristics includes at least one edit heuristic that, when applied to the query molecule specification, adds a Nitrogen or a substituent to the query molecule specification, removes a Nitrogen or a substituent from the query molecule specification, or repositions a substituent included in the query molecule specification to generate a derived molecule specification.

16. The one or more non-transitory computer readable media of claim 11, wherein the plurality of edit heuristics includes at least one edit heuristic that, when applied to the query molecule specification, replaces an Oxygen included in the query molecule specification with a Sulfur or replaces a Sulfur included in the query molecule specification with an Oxygen.

17. The one or more non-transitory computer readable media of claim 11, wherein the one or more mapping operations map the plurality of derived molecule specifications to a vector space to generate the plurality of mapped molecule specifications.

18. The one or more non-transitory computer readable media of claim 11, wherein performing the one or more hash-based search operations comprises performing a hash-based search on the mapped catalog of molecules based on a first mapped molecule specification included in the plurality of mapped molecule specifications to determine that a first derived molecule specification include in the plurality of derived molecule specifications matches a first molecule specification included in the mapped catalog of molecules.

19. The one or more non-transitory computer readable media of claim 11, wherein the query molecule specification represents a drug development candidate of interest associated with the drug discovery process.

20. A system comprising:

one or more memories storing instructions; and one or more processors coupled to the one or more memories that, when executing the instructions, perform the steps of:

generating a plurality of likelihoods by determining, for each edit heuristic included in a plurality of edit heuristics, a likelihood that a target bioactivity associated with a query molecule specification is preserved when the edit heuristic is applied to the query molecule specification, wherein each edit heuristic included in the plurality of edit heuristics specifies a different type of modification to a structure of an existing molecule;

generating a subset of the plurality of edit heuristics based on the plurality of likelihoods;

applying the subset of the plurality of edit heuristics to the query molecule specification to generate a plurality of derived molecule specifications;

performing one or more mapping operations on the plurality of derived molecule specifications to generate a plurality of mapped molecule specifications that are compressed digital representations of the plurality of derived molecule specifications;

performing one or more hash-based search operations on a mapped catalog of available molecules that can be acquired based on the plurality of mapped molecule specifications to determine one or more potential drug candidates; and causing one or more search results that include the one or more potential drug candidates to be outputted.

* * * * *